US00PP35905P2

(12) United States Plant Patent
Knapp et al.

(10) Patent No.: US PP35,905 P2
(45) Date of Patent: Jul. 2, 2024

(54) STRAWBERRY PLANT NAMED 'UC MONARCH'

(50) Latin Name: ***Fragaria* x *ananassa* Duchesne.**
Varietal Denomination: UC Monarch

(71) Applicant: The Regents of the University of California, Oakland, CA (US)

(72) Inventors: Steven J. Knapp, Davis, CA (US); Glenn S. Cole, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 18/135,707

(22) Filed: Apr. 17, 2023

(51) Int. Cl.
*A01H 5/08* (2018.01)
*A01H 6/74* (2018.01)

(52) U.S. Cl.
USPC ..... Plt./208

(58) Field of Classification Search
USPC ..... Plt./208
CPC ... A01H 5/08; A01H 5/00; A01H 6/74; A01H 6/7409
See application file for complete search history.

(56) References Cited

U.S. PATENT DOCUMENTS

PP26,709 P3 * 5/2016 Larson ..... A01H 5/08 Plt./208
PP32,950 P3 * 4/2021 Knapp ..... A01H 5/08 Plt./208
PP32,966 P3 * 4/2021 Knapp ..... A01H 5/08 Plt./208

OTHER PUBLICATIONS

Cal Poly Strawberry Center 2021 Strawberry Field Day retrieved on Aug. 24, 2023 at https://content-calpoly-edu.s3.amazonaws.com/strawberry/1/images/Final%20Field%20Day%20Handouts%20Booklet207.26.21%20CS_FV_reduced%20file%20size.pdf, 2 cover pages, pp. 1-3, 19-22. (Year: 2021).*
Cal Poly Strawberry Center 2022 Strawberry Field Day, retrieved online at https://content-calpoly-edu.s3.amazonaws.com/strawberry/1/images/2022Field DayBooklet-FINAL-07_22_22-PM-comp.pdf, 6 introductory pages pp. 20-29. (Year: 2022), 16 pp. total.
See information in accompanying Information Disclosure Statement letter, 8 pp.
See information in accompanying Information Disclosure Statement letter, 7 pp. 2020-1017 and 8 pp. 2020-1018.

* cited by examiner

*Primary Examiner* — June Hwu
(74) *Attorney, Agent, or Firm* — Kilpatrick Townsend & Stockton LLP

(57) ABSTRACT

'UC Monarch' is a 'short-day' cultivar strawberry plant that has an unusual long-truss plant architecture, provides high yields of firm flavorful, long shelf-life fruit, and has resistance to various soil-borne pathogens.

2 Drawing Sheets

Genus and species: The strawberry plant of this invention is botanically known as *Fragaria* x *ananassa* Duchesne.

Variety denomination: The variety denomination is 'UC Monarch'.

BACKGROUND

This invention relates to a new and distinct short-day cultivar of strawberry designated as 'UC Monarch', which originated from a cross performed in the winter of 2017. The plant of this selection was originally designated '17C138P021' for testing.

BRIEF SUMMARY

'UC Monarch' is a short-day cultivar that originated in the winter of 2017 from a cross between 'UCD Moxie' (U.S. Plant Pat. No. 32,953) and 'UCD Warrior' (U.S. Plant Pat. No. 32,950. Clones (daughter plants) of 'UC Monarch' were initially propagated from a single mother plant in 2017-

2018. 'UC Monarch' has since been preserved by annual cycles of asexual propagation from stolons in a facility at Winters, California.

'UC Monarch' was selected from a full-sib family (17C138) generated from the cross between 'UCD Moxie' and 'UCD Warrior'. It is unknown which is the female parent and which is the male parent. 'UC Monarch' shares the same parents with 'UC Keystone' (U.S. Plant patent application Ser. No. 18/135,708, filed Apr. 17, 2023). Seeds of the 17C138 family were produced and harvested in the spring of 2017 and germinated in June 2017. Seedlings were transplanted to a greenhouse in July 2017, hardened off in a shade house in August 2017, and transplanted to the field in September 2017. 'UC Monarch' was one of 10,000 individual hybrid plants from 359 full-sib families that were grown in 2017-18. The population was visually phenotyped in the spring of 2018 to: (a) identify individuals with outstanding fruit size, firmness, symmetry, color, gloss, and visual appeal; (b) eliminate individuals with fruit defects and deformities; (c) estimate marketable fruit yields; (d) identify putative photoperiod insensitive individuals; (e) assess stolon proliferation (runner production) and plant architecture; and (f) select individuals for clonal multiplication and further testing. Fifty-six individuals from the 2017-18 selection cycle were selected for on-farm advanced testing (Phase I, II, and III) in Oxnard and Santa Maria California. Disease resistance of the selections was tested in Davis, California.

'UC Monarch' has a long-truss plant architecture and differs from the closest comparison varieties as follows: The length of the flowering trusses is longer then both parents. 'UCD Monarch' also has improved tolerance to Macrophomina compared to 'UCD Moxie', which is susceptible; and has moderate resistance to Verticillium wilt compared to 'UCD Warrior', which is moderately susceptible. 'UCD Monarch' fruit are smaller than those of 'UC Surfline' (U.S. Plant patent application Ser. No. 18/135,711, filed Apr. 17, 2023), 'UCD Victor' (U.S. Plant Pat. No. 32,966), and 'Fronteras' (U.S. Plant Pat. No. 26,709); and are significantly firmer than 'Fronteras'. The titratable acidity was significantly lower for 'UC Monarch' than UC 'Surfline', 'UCD Victor', and 'Fronteras'.

'UC Monarch' was genotyped with a 50,000-SNP array (Hardigan et. al., *Frontiers in Plant Science* 10:1789, 2020; Hardigan et al., *Mol. Biol. Evol.* 38:2285-2305, 2021) that included 72 cultivars owned by the University of California and 300 publicly available cultivars not owned by the University of California. After quality- and LD-pruning, 31,212 SNP markers with well-separated codominant genotypic clusters were selected for further analysis. These analyses confirmed that 'UC Monarch' is genetically distinct from its parent varieties, and comparison varieties 'UC Surfline','UCD Victor', and 'Fronteras', as well as all of the other cultivars evaluated.

BRIEF DESCRIPTION OF THE DRAWINGS

The colors in the photograph are depicted as nearly true as is reasonably possible to obtain in color reproductions of this type.

DETAILED DESCRIPTION

Botanical Description

Figure 1:
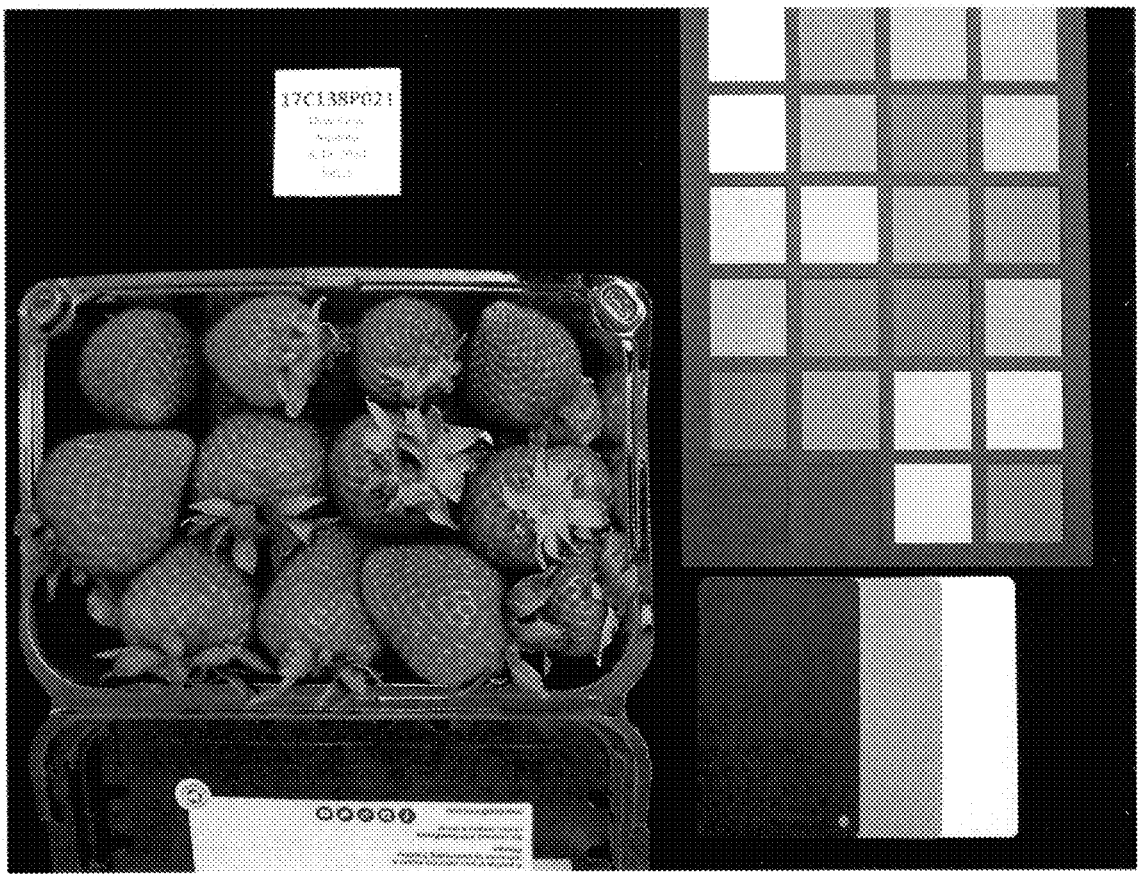
FIG. 1 depicts fruit of 'UC Monarch'.
Figure 2:
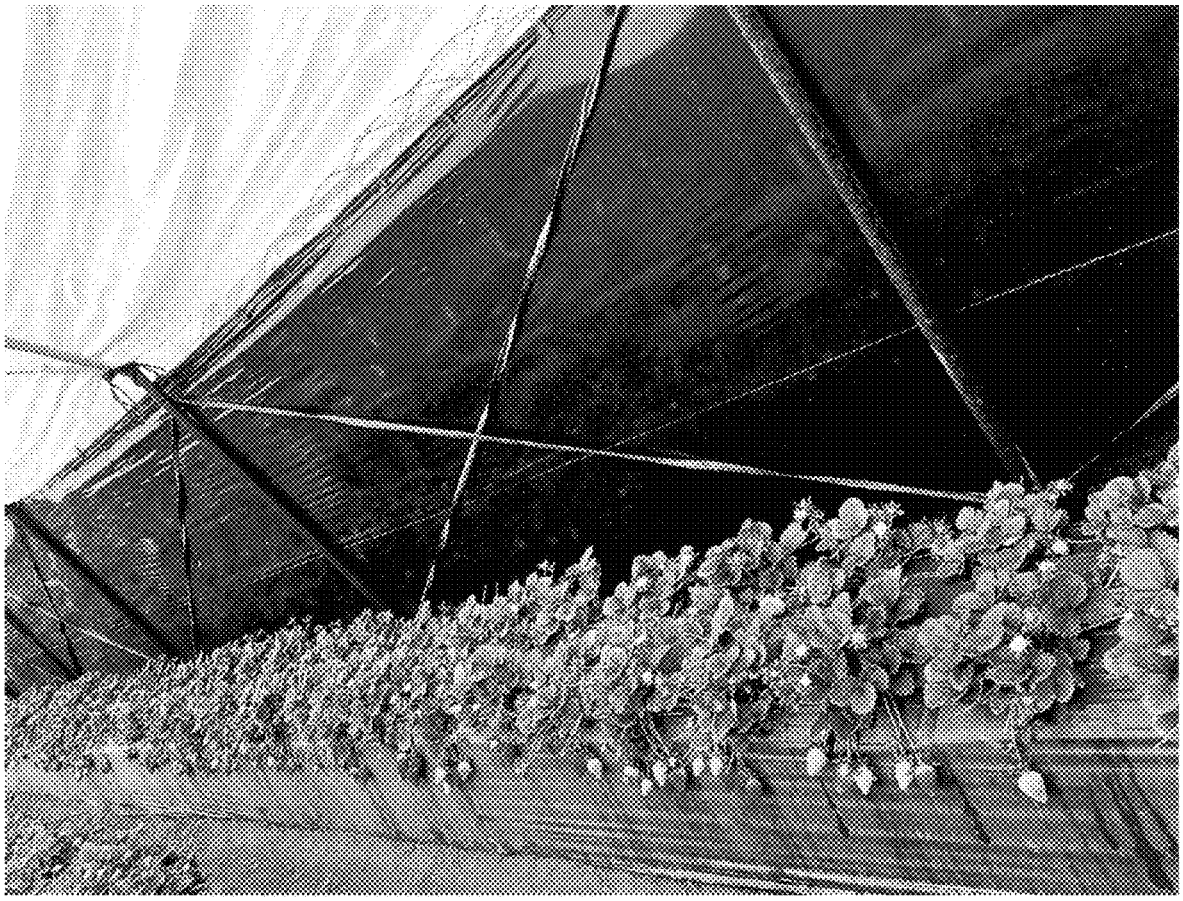
FIG. 2 shows 'UC Monarch' plants.

Botanical descriptors of 'UC Monarch' are provided in Table 1. The descriptors were collected in the spring and summer of 2022 from plants grown in Santa Maria, California. Colors are designated with reference to The Royal Horticultural Society (R.H.S.) Colour Chart, Sixth Edition, 2015. The characteristics of 'UC Monarch' may vary in detail, depending upon environmental factors and culture conditions.

TABLE 1

[a]Mean values were estimated from nine samples per trait.

| Category | Trait | Unit | Range (Mean[a]) or Color (RHS Colour Designation) |
|---|---|---|---|
| Foliar | Plant height | mm | 190-390(256) |
| Foliar | Plant spread | mm | 400-550(459) |
| Foliar | Plant habit | | Semi-upright |
| Foliar | Plant vigor | | Medium |

TABLE 1-continued

[a]Mean values were estimated from nine samples per trait.

| Category | Trait | Unit | Range (Mean[a]) or Color (RHS Colour Designation) |
|---|---|---|---|
| Foliar | Mid-tier terminal leaflet length | mm | 75-110(96) |
| Foliar | Mid-tier terminal leaflet width | mm | 100-140(118) |
| Foliar | Mid-tier terminal leaflet, margin type | | Serrate to Crenate |
| Foliar | Mid-tier terminal leaflet, base shape | | Obtuse |
| Foliar | Leaf, average size | | Medium |
| Foliar | Leaf, blistering | | Medium |
| Foliar | Leaf, glossiness | | Medium |
| Foliar | Petiole length | mm | 180-250(208) |
| Foliar | Petiole attitude of hairs | | Horizontal |
| Foliar | Petiole, color | color code | Strong Yellow Green (145 A) |
| Foliar | Stipule core color | color code | Strong Yellow Green (144 B) |
| Foliar | Stipule margin color | color code | Strong Yellow Green (144 A) |
| Foliar | Stolons/nursery mother plant | count | 12-14(13) |
| Foliar | Stolon color | color code | Moderate Pink (51 D) |
| Foliar | Stolon, average length | m | 1 meter |
| Foliar | Stolon, surface texture | | Smooth |
| Foliar | Leaf color, adaxial | color code | Greyish Olive Green (NN137 A) |
| Foliar | Leaf color, abaxial | color code | Moderate Yellow Green (147 B) |
| Foliar | Inflorescence, position in relation to foliage | | Above |
| | Pedicel, average length | cm | 40 |
| | Pedicel, attitude of hairs | | Upwards |
| Flower | Petal number | count | 5-6(6) |
| Flower | Petal length | mm | 7-15(11) |
| Flower | Petal width | mm | 7-15(11) |
| Flower | Petal arrangement | | Overlapping |
| Flower | Calyx diameter | mm | 27-46(37) |
| Flower | Corolla diameter | mm | 24-35(30) |
| Flower | Sepal number | count | 10-13(11) |
| Flower | Calyx Color | color code | Moderate Olive Green (137 A) |
| Flower | Upper Petal Color | color code | White (NN155 D) |
| Flower | Lower Petal Color | color code | White (NN155 D) |
| Flower | Stamen number | count | 24-30(27) |
| Fruit | Achene Color | color code | Greenish Brilliant Yellow (4 A) |
| Fruit | Fruit length | mm | 35-50(43) |
| Fruit | Fruit width | mm | 27-40(33) |
| Fruit | Fruit size | | Large |
| Fruit | Fruit shape | | Conical |
| Fruit | Fruit evenness of color | | Even or slightly uneven |
| Fruit | Fruit glossiness | | Medium |
| Fruit | Fruit, evenness of the surface | | Even or slightly uneven |
| Fruit | Fruit, width of band without achene | | Absent or narrow |
| Fruit | Fruit, attitude of sepals | | Upwards |
| Fruit | Fruit, position of achenes | | Below Surface |
| Fruit | Fruit, position of calyx attachment | | Inserted |
| Fruit | Fruit, adherence of calyx to fruit | | Very strong |
| Fruit | Size of hollow core | mm | 0-5(4) |
| Fruit | External Fruit (exterior) color | color code | Moderate Red (N45 A) & Vivid Red (45 A) |
| Fruit | Fruit flesh color | color code | Vivid Reddish Orange (33 A) |
| Fruit | Fruit core color | color code | Strong Reddish Orange (42 C) |
| Fruit | Fruit size | g/fruit | 19-32(25) |

In Oxnard, California, with an October planting time, early flowering is in January and the beginning of fruit ripening on those early flowers is 30 days post-flowering.

Disease Resistance

'UC Monarch' and comparison cultivars were phenotyped for resistance to Fusarium wilt, Verticillium wilt, Phytophthora crown rot (PhCR), and Macrophomina over three growing seasons in Davis, California. Hybrids were screened using bare-root plants (four clones/hybrid) that were artificially inoculated with a single pathogen, planted in fumigated ground in November, and phenotyped for disease symptoms in late spring and early summer using established protocols.

The disease resistance scores for 'UC Monarch' were primarily compared to those for 'UC Surfline', which had the best resistance scores among the comparison cultivars (Table 2). Estimated marginal means (EMMs), linear contrasts among EMMs for 'UC Monarch' and comparison cultivars ('Fronteras', 'UCD Victor', and 'UC Surfline'), and associated statistics from three seasons of disease screening in Davis, CA are shown in Table 2. The disease resistance scores for 'UC Monarch' were not significantly different from those of 'UC Surfline' across the board.

'UC Monarch' and the comparison cultivars were resistant to Fusarium wilt race 1 (Table 2). 'UC Monarch' is heterozygous for FW1, a dominant gene that confers resistance to race 1 isolates of *Fusarium oxysporum* f. sp. *fragariae*. This was confirmed using DNA markers in linkage disequilibrium with FW1 and validated by three years of field testing (Table 2).

'UC Monarch' is also resistant to Verticillium wilt, Phytophthora crown rot and Macrophomina. Scores for 'UC Monarch' for Verticillium wilt, Phytophthora crown rot, and Macrophomina charcoal rot resistance were similar to those for the comparison cultivars and have been the strongest observed among modern cultivars in our disease screening trials (Table 2).

The Macrophomina resistance score EMMs reported in Table 2 were estimated from phenotypes observed in a high heat and drought stress environment (Davis, CA). Although the resistance score EMM for 'UC Monarch' from abiotic stress environment was intermediate (3.62), this generally ranslates to a resistance score in the 1.5 to 2.5 range in coastal CA production environments. No Macrophomina disease symptoms were observed on 'UC Monarch' from natural Macrophomina infections in any of the on-farm trials. The Macrophomina resistance of 'UC Monarch' is as strong as that found in any commercially important short-day cultivar today.

TABLE 2

Across year estimated-marginal means (EMMs) for *Fusarium* wilt, *Verticillium* wilt, and *Phytophthora* crown rot (PhCR) resistance scores[a] for 'UC Monarch' and check cultivars observed in 2019-20, 2020-21, and 2021-22 disease resistance screening trials at Armstrong Farm, Davis, CA.

| Disease[b] | Check Cultivar | UC Monarch EMM | Check Cultivar EMM | t[c] | p-value[d] |
|---|---|---|---|---|---|
| *Fusarium* Wilt | Fronteras | 1.22 | 1.09 | 0.30 | 0.77 |
| | UCD Victor | | 1.09 | 0.31 | 0.75 |
| | UC Surfline | | 1.02 | 0.47 | 0.64 |
| | UCD Warrior | | 1.47 | −0.55 | 0.59 |
| | San Andreas | | 1.15 | 0.12 | 0.90 |
| *Verticillium* wilt | Fronteras | 1.79 | 1.71 | 0.18 | 0.86 |
| | UCD Victor | | 2.30 | −1.08 | 0.29 |
| | UC Surfline | | 1.62 | 0.39 | 0.70 |
| | UCD Warrior | | 2.56 | −1.65 | 0.10 |
| | San Andreas | | 1.29 | 0.72 | 0.47 |
| *Phytophthora* crown rot | Fronteras | 2.04 | 2.54 | −0.90 | 0.37 |
| | UCD Victor | | 2.19 | −0.27 | 0.79 |
| | UC Surfline | | 1.67 | 0.66 | 0.51 |
| | UCD Warrior | | 2.03 | 0.02 | 0.99 |
| | San Andreas | | 1.83 | 0.28 | 0.78 |
| *Macrophomina* Charcoal rot | Fronteras | 3.62 | 4.16 | −0.84 | 0.40 |
| | UCD Victor | | 4.50 | −1.38 | 0.17 |
| | UC Surfline | | 3.61 | 0.03 | 0.98 |
| | UCD Warrior | | 3.78 | −0.25 | 0.81 |
| | San Andreas | | 4.71 | −1.23 | 0.22 |

[a]The ordinal symptom rating scales were identical for each disease: 1 = highly resistant, 2 = moderately resistant, 3 = moderately susceptible, 4 = susceptible, and 5 = highly susceptible.
[b]The fungal pathogens causing these diseases are *Fusarium oxysporum* f. sp. *fragariae* (*Fusarium* wilt), *Verticillium dahliae* (*Verticillium* wilt), *Phytophthora cactorum* (*Phytophthora* crown rot).
[c]t-statistics for linear contrasts ($EMM_1 - EMM_2$) between the EMMs for 'UC Monarch' and check cultivars.
[d]The probability of a greater t-statistic by chance for tests of the null hypothesis of no difference between EMMs ($H_0$: $EMM_1 = EMM_2$).

Field Evaluations

Three seasons of advanced testing of selected short-day hybrids originating from the 2016-17 breeding cycle, starting with fifty-six in 2018-19 and finishing with three in 2020-21, one of which was 'UC Monarch', were completed. Comparison cultivars were 'Fronteras', 'UCD Victor'' and 'UC Surfline'.

Clones (asexually propagated bare-root plants) for the first year of testing (Phase 1 in 2018-19) were produced in Winters, California. Clones for subsequent years of testing (Phase 2 in 2019-20, 2020-21, and 2021-22 and Phase 3 in 2022-23) were produced in commercial high-elevation nurseries (Dorris, California) using standard production and propagation practices and post-harvest chilling treatments optimized for the day-neutral market segment. Clones were harvested in September, trimmed, and directly planted in October of each year.

For on-farm yield trials, plants were grown in two 12-plant plots in Phase 1 yield trials, two 24-plant plots in Phase 2 yield trials, and two 500- or 1,000-plant strip in Phase 3 yield trials. The plots were arranged in randomized complete blocks experiment designs in commercial production fields. These experiments were grown using the management practices, bed configurations, plastic mulches, planting densities, planting dates, irrigation, fertilization, and pesticide application decisions and schedules, and harvest schedules of our cooperators.

The number of harvests ranged from 14 to 37 in each yield trial. Marketable fruit yield, count, and size were recorded at each harvest. Collection and analysis of 4,695 observations were employed for these traits to support statistical analyses and selection decisions.

Fruit Quality

Fruit from early and peak season harvests from every trial were evaluated to phenotype fruit for firmness, total soluble solids (TSS=Brix), and titratable acidity (TA). Over three growing seasons, 2,240 observations were collected for fruit quality traits at harvest to support statistical analyses and selection decisions.

Plants were assessed for flavor and aroma through informal hedonic testing in the field and laboratory by various individuals, including growers, shippers, and others. Although specific volatile organic compounds (VOCs) known to affect aroma were not selected for, selection pressure for enhanced flavor and aroma was applied and VOC profiles were analyzed for 152 cultivars and other hybrids over two years of on-farm testing. 'UC Monarch' was among the hybrids phenotyped for VOC). These data were used to assess the effect of subjective olfactory and gustatory assessments on aroma profile changes. VOC analyses were performed using solid phase microextraction (SPME) gas chromatography-mass spectroscopy of fruit samples collected from early and peak season harvests over two years from on-farm yield trials in Santa Maria, California. Although at least 360 VOCs have been identified in developing strawberry receptacles, aroma and flavor are dominated by fewer than 10. Data for approximately 44 VOCs affecting aroma (45,364 phenotypic observations) were collected and analyzed to support statistical analyses. Data for three VOCs (γ-decalactone, mesifurane, and linalool) that are predicted to contribute towards the improved flavor of 'UC Monarch' are provided.

Table 3 provides estimated marginal means (EMMs), linear contrasts among EMMs for 'UC Monarch' and comparison cultivars ('Fronteras', 'UCD Victor', and 'UC Surfline'), and associated statistics within and between environments (2 locations×3 years).

TABLE 3

Across-environment estimated marginal means (EMMs) for cumulative marketable fruit yield and other fruit traits for 'UC Monarch' and comparison cultivars grown on commercial farms in Oxnard and Santa Maria, CA over three growing seasons (2019-20 to 2021-22)[a].

| Trait[a] | Comparison Cultivar | UC Monarch EMM | Comparison Cultivar EMM | t[b] | p-value[c] |
|---|---|---|---|---|---|
| Yield (lb/acre) | Fronteras | 35,707 | 38,833 | −0.68 | 0.51 |
| | UCD Victor | | 40,874 | −1.11 | 0.29 |
| | UC Surfline | | 46,865 | −2.43 | 0.03 |
| Size (g/fruit) | Fronteras | 25.6 | 32.4 | −4.73 | 0.0003 |
| | UCD Victor | | 29.6 | −2.72 | 0.02 |
| | UC Surfline | | 29.5 | −2.69 | 0.02 |
| Firmness (g-force) | Fronteras | 307.4 | 225.9 | 3.14 | 0.003 |
| | UCD Victor | | 296.5 | 0.88 | 0.38 |
| | UC Surfline | | 339.1 | −1.22 | 0.23 |
| TSS (%) | Fronteras | 7.73 | 8.66 | −3.06 | 0.004 |
| | UCD Victor | | 7.89 | −1.01 | 0.32 |
| | UC Surfline | | 8.18 | −1.50 | 0.14 |
| TA (%) | Fronteras | 0.70 | 0.86 | −4.45 | <0.0001 |
| | UCD Victor | | 0.76 | −3.22 | 0.002 |
| | UC Surfline | | 0.86 | −4.58 | <0.0001 |
| TSS/TA | Fronteras | 11.00 | 10.44 | 0.97 | 0.34 |
| | UCD Victor | | 10.47 | 1.73 | 0.09 |
| | UC Surfline | | 9.82 | −2.04 | 0.05 |

[a]Cumulative marketable fruit yields were estimated from fruit harvested on commercial schedules (once or twice weekly) over the entire short-day growing season on each farm. Fruit firmness, to- tal soluble solids (TSS), and titratable acidity (TA) were measured from multiple fruit/replication sampled from two harvests/trial. EMMs and test statistics were estimated from the phenotypes of fruit harvested from two 24-plant plots/entry/environment.
[b]t-statistics for linear contrasts ($EMM_1 - EMM_2$) between 'UC Monarch' and check cultivar EMMs.
[c]The probability of a greater t-statistic by chance for tests of the null hypothesis of no difference between EMMs ($H_0$: $EMM_1 = EMM_2$). item[d] Yield prior to March 1st.

'UC Monarch' fruit were smaller than those of the other comparison cultivars across years and locations (p-values ranged from 0.02 to 0.003). 'UC Monarch' fruit were significantly firmer than 'Fronteras' but not significantly different from the other two comparison cultivars (Table 3).

The ratio of total soluble solids to titratable acidity (a perceived 'sweetness' metric) was significantly greater for 'UC Monarch' than 'UC Surfline' (Table 3). The titratable acidity was significantly lower for 'UC Monarch' than the three comparison cultivars, which improved the perceived sweetness of this cultivar. This was confirmed in pre-commercial testing on several farms.

The aroma of 'UC Monarch' is more pronounced than that of the three comparison cultivars (especially 'Fronteras' and 'UCD Victor') (Table 4). GC-MS analyses show that the concentrations of three important aroma compounds (γ-decalactone, mesifurane, and linalool) appear to be elevated in 'UC Monarch' (Table 4). These three compounds contribute to the improved flavor and aroma of 'UC Monarch'.

TABLE 4

Across-year estimated-marginal means (EMMs)[a] for γ-decalactone, mesifurane, and linalool concentrations[a] in ripe fruit of 'UC Monarch' and comparison cultivars harvested in 2020-21 and 2021-22 from on-farm yield trials in Nipomo, CA.

| Cultivar | γ-decalactone EMM | mesifurane EMM | linalool EMM |
|---|---|---|---|
| Fronteras | 0 | 0 | 0 |
| UCD Victor | 0 | 4,181 | 100,499 |
| UC Monarch | 36,429 | 23,660 | 65,017 |
| UC Surfline | 7,555 | 2,792 | 93,371 |
| LSDb | 42,528 | 18,116 | 66,721 |

[a]The relative concentrations of volatile organic compounds (ng/g dry weight) were estimated from the raw solid phase microextraction (SPME) GC-MS data (peak area in counts) and normalized samples.
[b]Least significant differences are shown for a false-positive probability of p = 0.05.

Fruit Production Characteristics—Field Trials

The number of harvests ranged from 14 to 37 in each trial to assess 'UC Monarch' fruit production. Marketable fruit yield, count, and size were recorded at each harvest. Collection and analysis of 4,695 observations were performed for these traits to support statistical analyses.

Statistics are shown for linear contrasts between the estimated marginal means (EMMs) for 'UC Monarch', and comparison cultivars across environment (2 locations×3 years) and for individual environments to highlight variation in planting dates, the number of harvests, harvest ranges, and production practices (Table 5). EMMs were estimated from two 24-plant plots (replications)/entry/environment in 2020 and 2021.

TABLE 5

Within environment estimated marginal means (EMMs) for cumulative marketable fruit yield for 'UC Monarch' and comparison cultivars grown on farms in coastal California over three growing seasons (2020-21 to 2021-22)[a].

| Location | Season | Check Cultivar | 'UC Monarch' EMM (lb/a) | Check Cultivar EMM (lb/a) | t[b] | p-value[c] |
|---|---|---|---|---|---|---|
| Oxnard | 2020-21 | Fronteras | 45,894 | 46,248 | −0.04 | 0.97 |
| | | UCD Victor | | 59,689 | −1.48 | 0.24 |
| | | UC Surfline | | 64,048 | −1.95 | 0.15 |
| Santa Maria | 2020-21 | Fronteras | 46,220 | 53,563 | −1.35 | 0.27 |
| | | UCD | | 52,280 | −1.12 | 0.35 |

TABLE 5-continued

Within environment estimated marginal means (EMMs) for cumulative marketable fruit yield for 'UC Monarch' and comparison cultivars grown on farms in coastal California over three growing seasons (2020-21 to 2021-22)[a].

| Location | Season | Check Cultivar | 'UC Monarch' EMM (lb/a) | Check Cultivar EMM (lb/a) | t[b] | p-value[c] |
|---|---|---|---|---|---|---|
| Oxnard | 2021-22 | Victor | 13,026 | 52,241 | −1.11 | 0.35 |
| | | UC Surfline | | 19,386 | −11.56 | 0.001 |
| | | Fronteras | | 13,810 | −1.42 | 0.25 |
| | | UCD Victor | | 17,496 | −8.12 | 0.003 |
| Santa Maria | 2021-22 | UC Surfline | 31,097 | 32,138 | −0.12 | 0.91 |
| | | Fronteras | | 25,420 | 0.64 | 0.57 |
| | | UCD Victor | | 48,894 | −1.89 | 0.16 |
| | | UC Surfline | | | | |

[a]Linear contrasts between estimated marginal means (EMMs) for 'UC Monarch' and check cultivars were estimated for each environment. Cumulative marketable fruit yields were estimated from fruit harvested on commercial schedules (once or twice weekly) over the entire short-day growing season on each farm. EMMs and test statistics were estimated from the phenotypes of fruit harvested from two 24-plant plots/entry.
[b]t-statistics for linear contrasts ($EMM_1 - EMM_2$) between the EMMs for 'UC Monarch' and check cultivars.
[c]The probability of a greater t-statistic by chance for tests of the the null hypothesis of no difference between EMMs ($H_0$: $EMM_1 = EMM_2$).

The yield of 'UC Monarch' was not significantly different from 'Fronteras' or 'UCD Victor' across locations and years (Table 5). The yield of 'UC Monarch' was significantly lower than 'UC Surfline' across years and locations. The yield data for Oxnard in 2021-22 were anomalous because the grower elected to stop harvesting much earlier than normal. The yield for 'UC Monarch' was significantly lower than 'Fronteras' in that environment, but not in the other years and locations (Table 5).

Fruit of 'UC Monarch' has a post-harvest shelf life of greater than 21 days when stored at 34°-36° F. before fruit degradation begins.

'UC Monarch' is thus a highly productive disease resistant short-day cultivar with a long-truss plant architecture promising for robotic harvesting and production in unconventional protected culture growing systems. 'UC Monarch' can be used for fresh market and processing purposes.

What is claimed is:

1. A new and distinct cultivar of strawberry plant named 'UC Monarch', substantially as described and illustrated herein.

* * * * *

17C138P021